US006613002B1

(12) United States Patent
Clark et al.

(10) Patent No.: US 6,613,002 B1

(45) **Date of Patent: *Sep. 2, 2003**

(54) SYSTEM OF INDICIA FOR A MEDICAL DEVICE

(75) Inventors: Tamisha A. Clark, Pfefftown, NC (US); Melvin Kem Hawkins, Bloomington, IN (US); John A. Karpiel, Winston-Salem, NC (US)

(73) Assignee: Wilson-Cook Medical Incorporated, Winston-Salem, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 45 days.

(21) Appl. No.: 09/587,301

(22) Filed: Jun. 5, 2000

Related U.S. Application Data

(60) Provisional application No. 60/137,824, filed on Jun. 5, 1999.

(51) Int. Cl.[7] .................................................. A61B 5/103

(52) U.S. Cl. ....................... 600/593; 600/104; 600/117; 600/585; 600/587; 604/164.13

(58) Field of Search ................................ 604/117, 528, 604/164.13; 600/104, 106, 107, 117, 587, 593

(56) References Cited

U.S. PATENT DOCUMENTS

| | | | |
|---|---|---|---|
| 4,464,175 A | * 8/1984 | Altman et al. | 600/116 |
| 4,774,948 A | 10/1988 | Markham | |
| 5,084,022 A | 1/1992 | Claude | |
| 5,209,730 A | 5/1993 | Sullivan | |
| 5,241,970 A | 9/1993 | Johlin, Jr. et al. | |
| 5,320,602 A | 6/1994 | Karpiel | |
| 5,343,874 A | 9/1994 | Picha et al. | |
| 5,379,779 A | 1/1995 | Rowland et al. | |
| 5,409,004 A | 4/1995 | Sloan | |
| 5,599,300 A | 2/1997 | Weaver et al. | |
| 5,843,028 A | 12/1998 | Weaver et al. | |
| 5,882,293 A | * 3/1999 | Ouchi | 600/104 |

FOREIGN PATENT DOCUMENTS

| | | |
|---|---|---|
| EP | 0519214 | 12/1992 |
| EP | 0723786 | 7/1996 |
| WO | 9639077 | 12/1996 |

OTHER PUBLICATIONS

Protector® Plus Wire Guide; Wilson–Cook® Medical Inc.; Catalog; Wire Guides; p. 4.

Trace® Hybrid; Wilson–Cook® Medical Inc.; Wire Guides; p. 5.

Tracer® Hybrid; Wilson–Cook® Medical Inc.; Catalog; Wire Guides; p. 1A–8.

* cited by examiner

*Primary Examiner*—John Mulcahy

(74) *Attorney, Agent, or Firm*—Brinks Hofer Gilson & Lione

(57) ABSTRACT

The present invention involves a elongated member, such as a wire guide, that is used with in a endoscopic procedure. In one aspect of the invention, the elongate member includes a first system of indicia comprising a scale reference markings that can include numeric indicia, sequentially increasing markers, etc., located at regular increments (e.g., 1 cm) on the distal portion of the elongate member, that permit measurement of structures within a body passage. In one example, an exchange wire guide having a radiopaque marker on the distal portion is positioned under fluoroscopy at a first location, such as the distal point of a stricture, and the scale reference marking on the wire guide that visible in the viewing region of the endoscope is read. The wire guide is partially withdrawn such that the marker corresponds to a second position (e.g., the proximal point of the stricture) and the new scale reference marking is read. The difference is calculated to determine the length of the structure. In a second aspect of the invention, a second system of indicia are included to aid the endoscopist in maintaining the device in position. These indicia, which may include oblique markings, helical striping, or some other closely spaced markings or pattern, help in the detection of longitudinal movement of the device.

23 Claims, 3 Drawing Sheets

25 10 29 12 11 30 59 16 15 53 28 27 14 13 26

SYSTEM OF INDICIA FOR A MEDICAL DEVICE

CROSS-REFERENCE TO RELATED APPLICATIONS

This application claims priority of provisional application Serial No. 60/137,824, filed Jun. 5, 1999.

TECHNICAL FIELD

This invention relates to minimally medical devices, more particularly, wire guides and related devices.

BACKGROUND OF THE INVENTION

It has been recognized that the placement of a series of markings on a surgical instrument such as a wire guide, catheter, needle, etc., can aid the physician in proper placement of the device in the body of a patient during a medical procedure. These markings can include bands, dots, lettering, numbering, colors, or other types of indicia to indicate position or movement of the device within the body. Visually distinguishable marks are often located at regular predetermined intervals, e.g., placement of one dot or band at the 5 cm mark, two dots or bands at 10 cm, etc. Such a system of indicia can be made to be visible under fluoroscopy by the use of certain radiopaque metals, or compounds incorporated into or printed on the device. When direct visualization is possible, numerical values imprinted on the device can be used as a scale for measuring structures or distance.

The ability to quantify distances or make measurements is the primary benefit that has inspired the development of marker systems for wire guides, catheters, and the like. Another use of markings is to provide a system whereby the clinician can determine relative movement of the device within the body. This has also been found to be useful in endoscopic procedures in which it is important to maintain a device at a stationary position or to detect relative movement of another component. An example is the use of an exchange wire guide which has a tendency to become displaced as catheters or other instrumentation are advanced or withdrawn over the wire guide. When these procedures are performed using an endoscope, the wire guide can be visualized and therefore, a pattern of markings to determine movement of the wire guide relative to the tip of the endoscope can help in restoring or maintaining proper position of the device. Spiral or helical markings have been used for this purpose; however, such a system cannot permit quantification of the amount of movement, or to make measurements in the body such as the length of a stricture or lesion in a duct or vessel. While scale indicia systems of markings are well known for wire guides and other minimally invasive medical devices, they usually involve fluoroscopic or other methods of measurement that rely on counting dots, bands, etc. to determine relative distances, often a difficult and imprecise method of measurement.

Direct visualization of indicia on the exchange wire guide via an endoscope offers some advantages; however, procedures such as accessing certain treatment sites such as the Papilla of Vater, mucous and other material can obscure the view, making direct measurement impossible. In addition, an exchange wire guide that is useful for measuring strictures for quantifying distance, can be inadequate for discerning movement when the visible area of the wire guide under endoscopy corresponds to gaps between markings. A system that permits endoscopic monitoring of the position of a wire guide to allow reliable and accurate measurement of anatomical structures is needed. Another desirable feature would be to combine the accurate measurement capabilities with a system that allows reliable detection of device movement during a medical procedure to assist in maintaining the device stationary.

SUMMARY OF THE INVENTION

The foregoing problems are solved and a technical advance is achieved in an illustrative embodiment of a exchange wire guide used with an endoscope, having multiple types of indicia for indicating position and/or movement within a body of a patient. In present invention, the elongated member, such a wire guide, e.g., a standard solid nitinol core, polymer-coated exchange wire catheter with a tapered or coil wire tip, or a catheter or some other medical device, includes a indicia pattern that is at least partially visible by direct or endoscopic observation. The indicia pattern comprises a first system and a second system of indicia. The first system of indicia includes series of scale reference markings that uniquely identify the particular distance to a fixed reference point on the elongate member, such as the distal tip. These scale references markings can consist of numerals, differently numbered bands, dots, etc., or some other form of unique indicia. The second system of indicia is imprinted on, or incorporated into the elongate member to allow the endoscopist or operator to readily determine whether the elongate member is moving relative to the endoscope into which it situated. The second system of indicia can comprise oblique lines, helical stripes, closely placed marking, or another pattern of indicia that allow one to detect longitudinal shifts in position by viewing the device through an endoscope or monitoring the external portion of the elongate member that extends proximally from the endoscope. Various embodiments of use of the second system of indicia include placement of oblique or closely spaced markings on the distal portion to be viewed by the endoscope, placement of the markings at the proximal portion of the elongate member such that they can be directly viewed externally of the patient to determine relative movement, or to incorporate the helical pattern into the device, e.g., providing a striped wire guide coating or co-extrusion of a bicolor catheter. In the case of the latter, the printed scale reference marker, bands, oblique lines, etc. can be printed over the surface of the device having the helical pattern.

In another aspect of the invention, numeric indicia are placed at selected intervals, e.g., 1 cm, along the distal portion of the wire guide such that they are viewable through an endoscope while the wire guide is positioned within a body passage, such as the gastrointestinal tract. The numerals advantageously provide a simple and accurate system for measurement of anatomical features within the body. The numeric indicia are optionally combined with differing numbered band or other non-numeric indicia at a larger interval, e.g., 5 cm. When the indicia pattern of the present invention is applied to an exchange wire guide, it permits the measurement of anatomical structures when used with an endoscope having an accessory channel for introducing ancillary devices or instrumentation. This obviates the need for separate measuring devices, and makes it especially useful for ERCP (Endoscopic Retrograde Cholangiopancreatography) procedures, when the length of a biliary stricture is to be measured. In one aspect of the invention configured for an ERCP procedure, the endoscope is advanced into the duodenum where the wire guide is then advanced from the distal end of the endoscope into the Papilla of Vater to access the biliary system. Further advancement of the endoscope tip into the common bile duct can often result in the operator's field of vision being obscured by mucous and/or body fluids. Instead, the tip of the endoscope remains in the duodenum where visibility is superior. To measure the stricture, the wire guide having a radiopaque marker on the distal portion is advanced until it has crossed the stricture. The wire guide tip is made visible by the use of a radiopaque material, either by loading the elastomeric material comprising the tip with a radiopaque material, such as a tungsten or barium powder, e.g., by a method such as that disclosed in U.S. Pat. No. 5,300,048 to Drewes; by addition of a second radiopaque material, such as applying radiopaque bands or shrink tubing, or dipped material; or by making the wire itself radiopaque, such as by placement of a platinum coil over a tapered solid core wire. In one example of how the present invention can be used, the clinician determines the numerical position of the wire guide using an endoscope, then withdraws the wire guide until the radiopaque tip marks the proximal boundary of the stricture. Calculation of the difference between the values observed on the wire guide gives the length of the stricture. This knowledge can be important in subsequent treatment, such as correct sizing of a biliary stent. Once the stricture has been measured, the wire guide can be maintained in place to serve as an exchange wire for introducing other instruments. Optionally, the second system of indicia is useful to the endoscopist in maintaining the wire guide stationary during such an exchange.

BRIEF DESCRIPTION OF THE DRAWINGS

Embodiments of the present invention will now be disclosed by way of example with reference to the accompanying drawings, in which.

DETAILED DESCRIPTION

Figure 4:
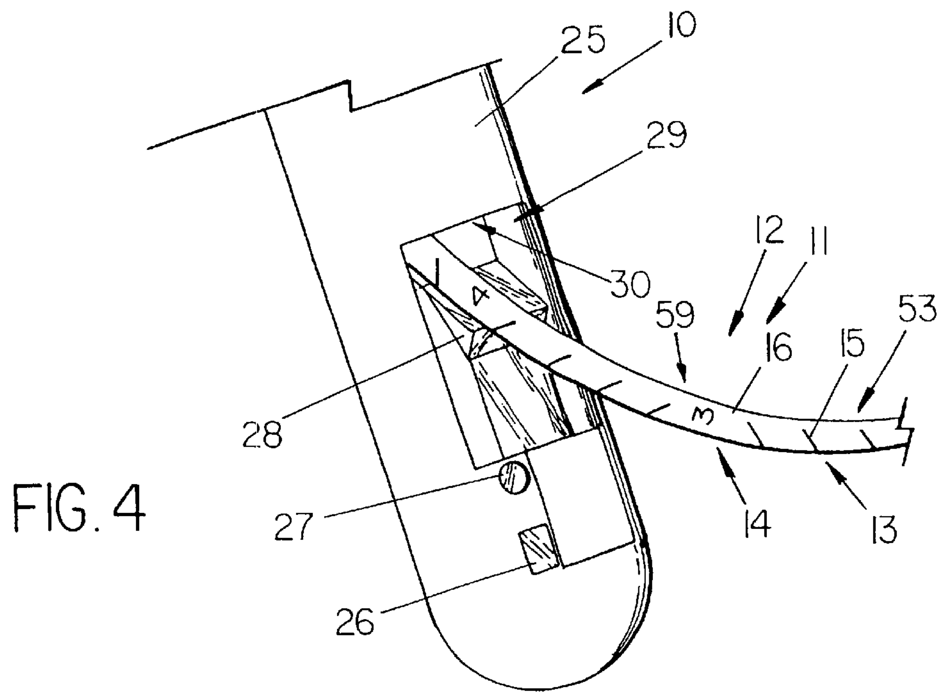
FIG. 4 depicts an enlarged pictorial view of the embodiment of FIG. 1 being used with an endoscope.
Figure 5:
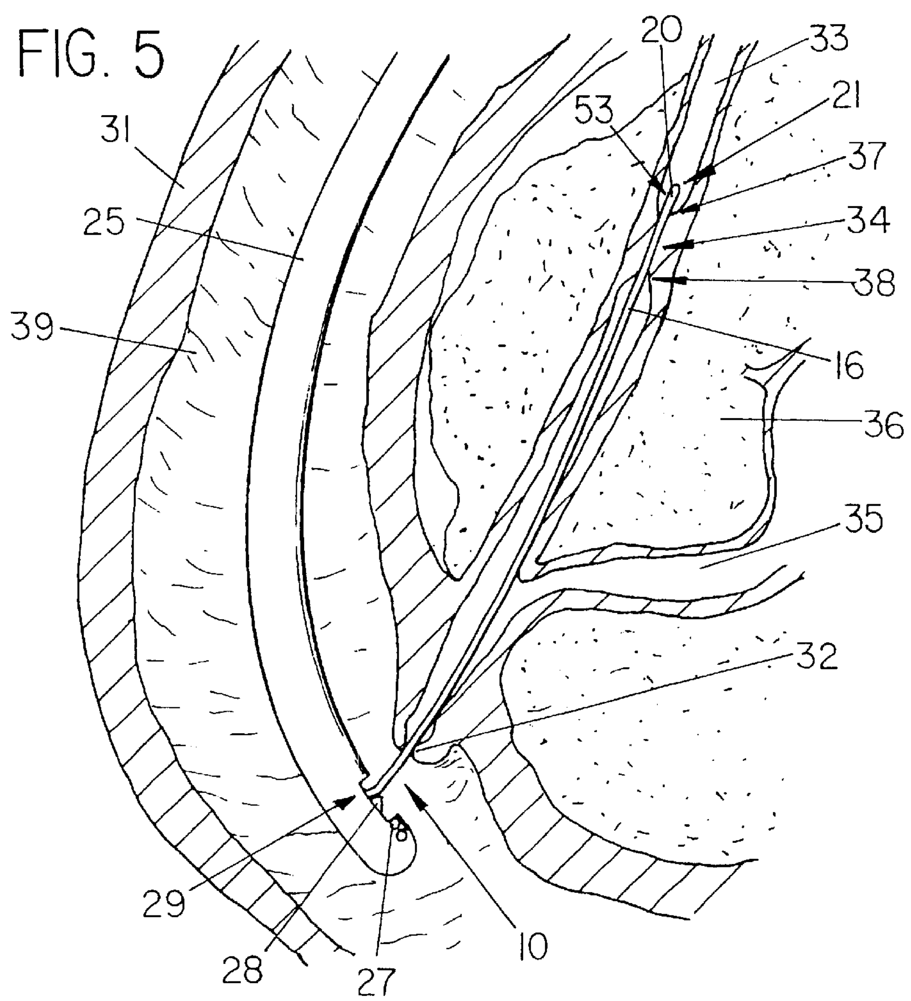
FIG. 5 depicts a view of the device being used in vivo.
Figure 6:
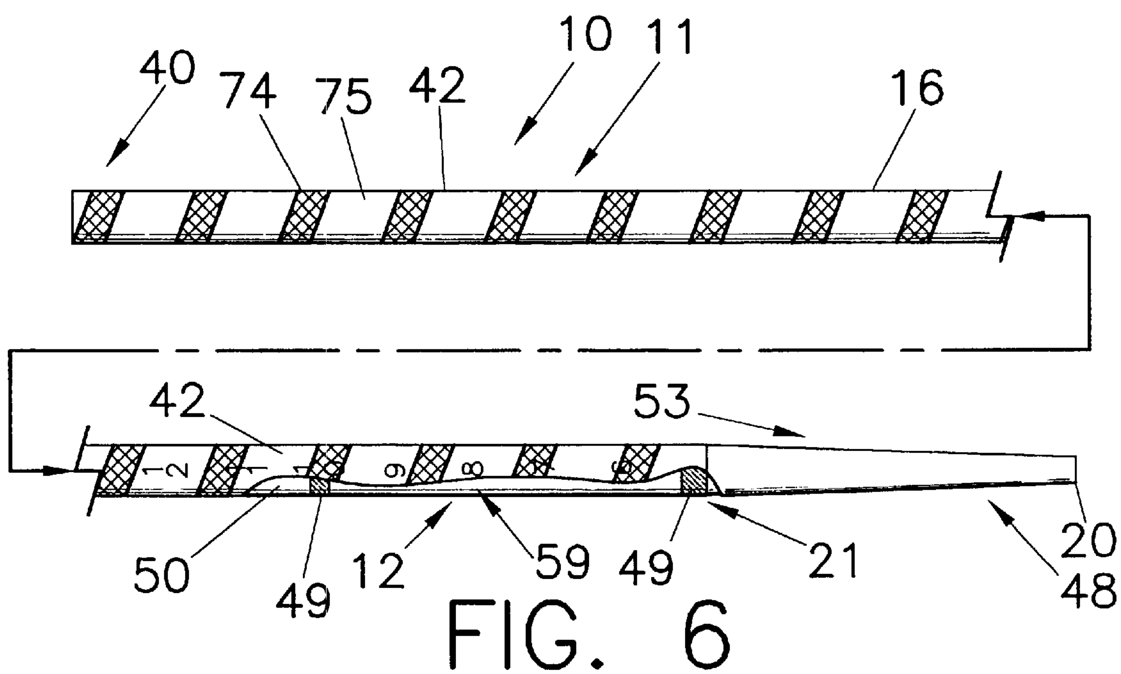
FIG. 6 depicts a partially sectioned side view of an alternative embodiment of the present invention.

FIGS. 1–6 depicts a medical device 10 comprising a wire guide 16 or similar elongate member having an indicia pattern 11 comprising a first and second system of indicia 12, 13 that allows the wire guide 16 to be used with an endoscope 25 to both measure anatomical structures within a patient using the first system of indicia 12, and maintaining the longitudinal position of the wire guide 16 using the second system of indicia 13. The illustrative device 10 preferably comprises a standard exchange wire guide 16, e.g., 480 cm or 260 cm in length, with a solid core wire 50, such as nitinol, and an outer surface coating 42, such as PET, that is shrink-wrapped over the wire as best shown in FIG. 6. To aid in fluoroscopic positioning of the wire guide 16, a distal portion of the device includes a radioactive marker material 21, either as a single marker, a plurality of markers, or an extended radiopaque region that is several centimeters long (e.g., the distal 5 cm). Different methods of providing radiopacity include standard techniques such as the addition of a distal platinum coil, adding gold or other radiopaque material markers, using radiopaque inks, or the use of radiopaque shrink wrap or tubing over the core wire, e.g., radiopaque urethane, or dipping the wire in a radiopaque polymer, or affixing a polymer tip, such as PEBAX®, that has been loaded with radiopaque powder, such as tungsten.

As shown in FIG. 4, the wire guide 16 includes a distal portion 53 designed to at least be partially advanced from the accessory or working channel 30 of an endoscope, the distal portion 53 including at least one of the first and second indicia patterns 12, 13. An intermediate portion 51, shown in FIG. 1, lies proximate to the proximal portion 51 that includes the first system of indicia. The intermediate portion 51, which may include a portion of the indicia pattern 11 such as the second system of indicia, largely remains withing the working channel of the endoscope during the main portion of the procedure. The proximal portion 40, depicted in FIG. 6, comprises the remainder of the wire guide 16 and is intended to substantially remain outside of the working channel of the endoscope. In the illustrative embodiment of FIG. 6, the proximal portion includes a portion of the second system of indicia 13, in the form of helical striping 74, 75, for helping the operator to better determine, via direct observation, whether the wire guide 16 is moving longitudinally.

In the embodiments of FIGS. 1–4, 6 the indicia pattern 11 comprises a first indicia pattern 12 that includes a series of unique scale reference markings 59 for permitting visual identification of the position of the wire guide 16 and quantifying distances of movement and lengths of anatomical structures. Preferably, these scale reference markings 59 correspond to standard scale increments for measuring distance (e.g., increments of 1 cm, 5 cm, 1 mm, 0.1 in., etc.). The scale reference markings 59 may refer to the distance to the distal tip 20, or some other point along the length of the device. In the illustrative embodiments, the scale reference markings 59 include numeric indicia 14 for this purpose. For example, a scale reference marking 59 of "8" might indicate that mark was 8 cm from the distal tip 20 of the wire guide 16, or it might indicate that it was 8 cm from another designated mark on the distal 53, intermediate 51, or proximal portion 40 of the wire guide 16.

Optionally, the scale reference markings 59 of the first system of indicia can include one or more unique series of non-numeric markings such as bands 41 at regular intervals along a portion of the device. The bands 41 are imprinted or applied to the wire guide as a separate material that can be radiopaque. In the illustrative embodiments, the bands increase (or decrease) in number to provide an additional second system of scale indicia to the numeric indicia 14.

A second system 13 of indicia is included to help determine relative movement of the wire guide 16. The second system of indicia 13 can include any combination of markings or structure of a configuration so that the operator can readily distinguish a portion of the second system of indicia 13 through an endoscope 25, as shown in FIG. 4, to determine that the medical device 10, such as a wire guide 16, is moving longitudinally relative to the endoscope. While this can be best accomplished by adding one or more helical or diagonal markings or components to the device, it can also be accomplished by a closely spaced series of marking whereby at least two adjacent marks always fall within the viewing field of the endoscope. Additionally, these closely spaced markings themselves can be circumferentially spiraled around the wire as a further visual cue. Helical or diagonal markings are particularly effective because the mark or markings appear to move circumferentially as well as longitudinally when the wire guide is being advanced or withdrawn. In the illustrative embodiments of FIGS. 1–6, the second system of indicia 13, comprises a series of markings such as diagonal lines 15, helical stripes 23, or circumferential marks, can be viewed on the wire guide 16 endoscopically to help the operator either maintain the device in place or determine the direction of movement. In the illustrative embodiments, the scale indicia 12 and second indicia 13 for movement are printed in ink on the outer coating 42 of the wire guide, which is a polymeric material such as PET, or another suitable material, although other well-known methods of imprinting or marking medical devices could be used. Optionally, the outer coating 42 of portions 40, 51 and 53 of the wire guide can comprise different materials. For example, the distal portion 53 can have a PET coating, which is more acceptable of printing, while the intermediate portion 51 and/or proximal portion 40 can be made of PTFE, which is more difficult on which to print. In another embodiment, the distal most portion of the distal portion 53 of the device, e.g., 5 cm, is advantageously made radiopaque by gluing on a separate tip, such as that made of PEBAX® loaded with a radiopaque powder, such as tungsten. In one embodiment, the tip contains a shoulder such that there is a smooth transition between the tip and the outer polymeric coating 42 which then overlays the shoulder. The tip is glued to the tapered section 48 of the core wire 50 (shown in FIG. 6) using cyanoacrylate or another suitable adhesive.

Additionally, an alternate type of first or second indicia 12, 13 is depicted in FIG. 6 that includes radiopaque markers such as radiopaque tubing 49 (e.g., radiopaque urethane) applied to the core wire 50 in distal portion 53 with the coating 42 placed thereover. As depicted, the radiopaque tubing 49 provides a series of radiopaque indicia at regular intervals that correspond to a known scale for determining length (e.g., 5 cm intervals).

Figure 1:
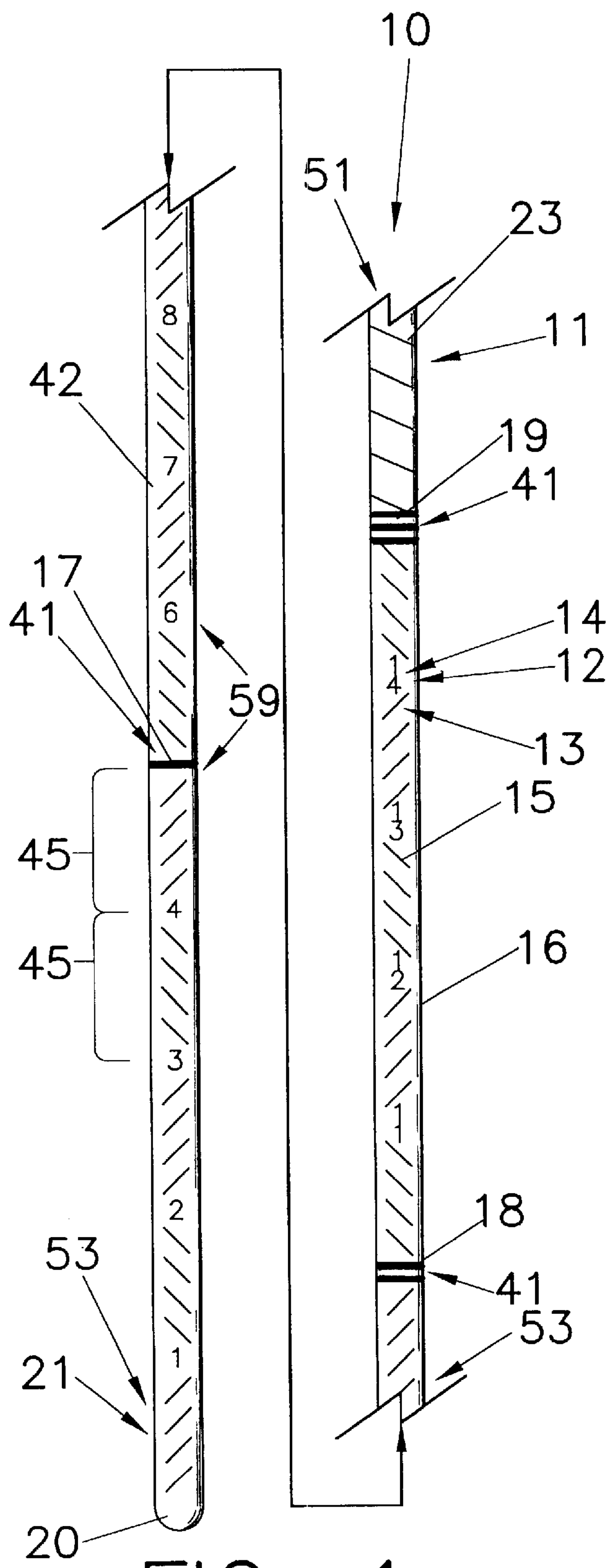
FIG. 1 depicts a side view of the illustrative embodiment of the present invention.

In the illustrative embodiment depicted in FIG. 1, the indicia pattern 11 on the distal portion 53 comprises a combination of scale reference markings 59 comprising numeric indicia 14 and differently numbered bands, and a second system of indicia 13 comprising oblique markings 15. A first scale reference marking 17 comprising single band 41 is located 5 cm from the distal tip 20 of the wire guide 16, while a second reference marking 18, comprising two adjacent bands, is located 10 cm from the distal tip 20. A third reference marking 19, comprising three bands, is located 15 cm from the distal tip 20. Of course, the series could continue in this manner for a longer distal portion 53. Between the series of bands 17, 18, 19 are numeric indicia 14, as depicted, however they could optionally include non-unique intermediate marking, e.g., single lines at each 1 cm increment between the 5 cm bands. Between the indicia 12, 41, is seen a second system of indicia 13 which comprises four diagonal lines 15 for aiding in determining the presence and direction of wire guide movement. At every 1 cm interval 45 of the illustrative embodiment, the direction of the diagonal lines 15 reverses as a further visual aid for determining wire guide position. To provide additional coverage around the circumference of the wire guide 16, the same indicia pattern 11 can be printed at 180° with respect to each other.

Figure 2:
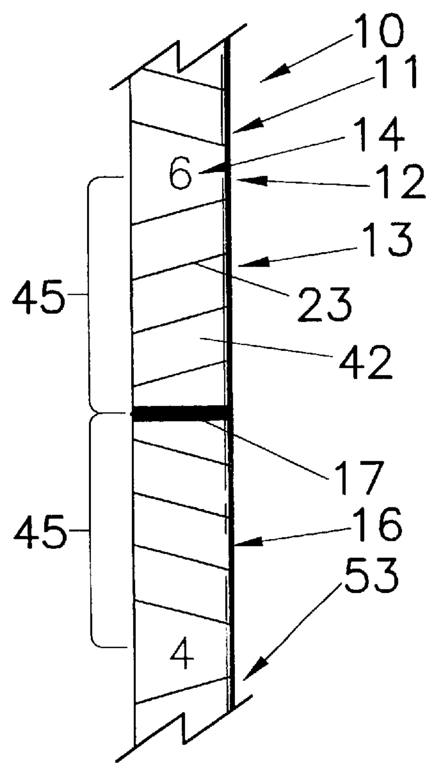
FIGS. 2–3 depicts enlarged side views of additional embodiments of the present invention.
Figure 3:
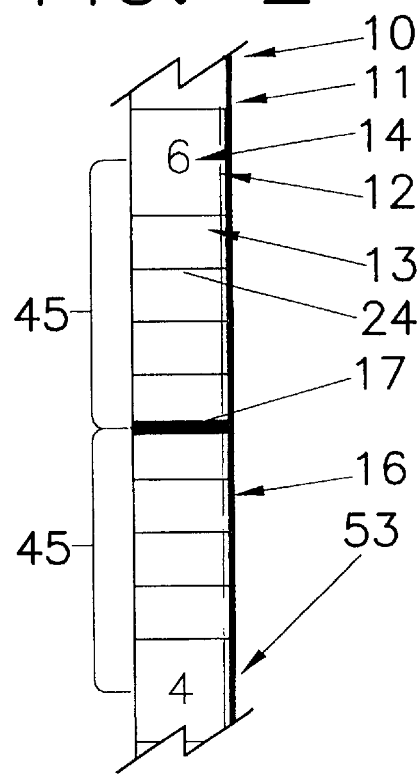

In the embodiment depicted in FIG. 2, the second system of indicia 13 includes helical stripes 23 that extend completely around the wire guide surface 42. FIG. 3 depicts still another embodiment wherein the second pattern of indicia 13 comprises a series of circumferential markings 24 for determining movement. Ideally, these are closely spaced such that at least one falls within the viewing region of the endoscope at all times. It should be noted that the first and second system of indicia can be functionally combined. For example, the first system of indicia 12 comprising the scale reference markings, can be longitudinally compressed by minimizing the increments (e.g., less than 1 cm) such that scale reference markings function as the second system of indicia 13 for indicating, relative movement. One example would be to have numeric indicia 14 at 1 or 5 mm increments ensure that multiple reference markings 59 would constantly be within the field of view, making it easier to visually detect movement. Additionally, these numeric indicia 14 could be spirally arranged, preferably with multiple helical series, to better indicate movement.

The 15 cm distal portion 46 in the embodiment of FIG. 1 can be extended, e.g., to 25 cm, if the wire guide is required to penetrate deeper into a duct or vessel. In addition, the proximal portion 40 of the illustrative wire guide (proximate to indicia 12, 14, 41) has an optional helical striping 23 imprinted on the wire guide surface 42 that helps determine movement of the device by looking at the portion extending proximally from the endoscope.

FIG. 6 depicts an embodiment of the second system of indicia 13 in which the outer coating 42 of the wire guide 16 includes helical striping whereby first and second contrasting colors 74, 55 alternately spiral down the length of the wire guide to add another visual cue to help distinguish relative movement of the device. This indicia pattern also can be used with the first system of indicia 12, as depicted in FIG. 6, or a different type of the second system of indicia 13, e.g., printed diagonal markings 15. In coiled wire guides that lack the outer polymer coating 42, a visually distinguishable helical coiled wired, e.g., of a different color, can be used as the second system of indicia 12 to distinguish relative motion, particularly in wire guides with multifilar coiled wire.

FIGS. 4–5 depict the wire guide 16 of the present invention being used with an endoscope 25. In FIG. 4, the wire guide 16 with indicia pattern 11 is positioned at the desired point at which the numerical value 14 can be read via the camera lens 27 under illumination of the light source 26. If it is desired to maintain a steady position of the wire guide 16, such as during a catheter exchange procedure, the diagonal lines 15 provide an means to determine whether the wire is moving and in which direction.

Now adding FIG. 5 to the discussion, the illustrative wire guide is especially useful in an ERCP procedure, for example, to measure a stricture 34 in the common bile duct 33 or another site within the biliary system, such as the pancreatic duct 35. The endoscope 25 is first advanced down into the duodenum to the Papilla of Vater 32, the entrance to the biliary system. The wire guide 16 is then advanced from the accessory channel 30 of the endoscope 25. The elevator 28 of the endoscope 25 is positioned to laterally deflect the wire guide 16 from the side opening 29 of the scope to facilitate advancement through the duct to the stricture 34. With the tip 20 of the wire guide 16 having a radiopaque component 21, the device is guided under fluoroscopy to the distal point 37 (furthest from the Papilla of Vater 32) 37 of the stricture 34. At that point, the numerical value 14 on the wire guide 16 is read through the camera lens 27 of the endoscope 25 as depicted in FIG. 4. After the first value has been determined, the wire guide 16 is withdrawn until the radiopaque tip 21 corresponds to the proximal point 38 (closest from Papilla of Vater 38) of the stricture 34. At that time, the wire guide 16 is reread endoscopically and the difference is calculated to determine the stricture 34 length. Following the measurement, a catheter or other device can be advanced over the same wire guide 16 which can facilitate the exchange of different devices.

It should be understood that although the illustrative embodiments include a wire guide having indicia, the indicia patterns described herein can be applied to any elongated medical device that might be used with an endoscope, such as a catheter, sphincterotome, or other related devices.

What is claimed is:

1. A medical device for measuring an anatomical structure comprising a first reference and a second reference within a body passage during a medical procedure which uses an endoscope, comprising:

an elongate member comprising a wire guide that includes a distal tip, a distal portion, and an indicia pattern, wherein the indicia pattern, which is at least partially located on the distal portion, includes a first system of indicia and a second system of indicia;

wherein the first system of indicia is located at least partially on the distal portion and includes a series of uniquely identifiable scale reference markings comprising at least two different types of markings, the wire guide so configured to be positionable within the endoscope such that when the distal portion is at least partially extended distally from the endoscope during the medical procedure, at least a portion of the first system of indicia is viewable to the operator with the endoscope while the distal portion of the wire guide as viewed with the endoscope is positioned relative to the first reference of the anatomical structure to obtain a first measurement, and at least a portion of the first system of indicia is viewable to the operator with the endoscope while the distal portion of the wire guide as viewed with the endoscope is positioned relative to the second reference of the anatomical structure, such that the anatomical structure within the body passage can be measured by comparing the first measurement to the second measurement;

wherein the second system of indicia includes a pattern of closely spaced markings so configured to readily indicate motion of the wire guide and spaced such that at least a portion thereof will fall within a viewable region located adjacent to an unsheathed portion of the wire guide during the medical procedure, the pattern of closely spaced markings located at least partially between selected ones of the scale reference markings.

2. The device of claim 1 wherein the wire guide includes a fixed reference point located therealong, wherein the first system of indicia includes a series of scale reference markings, each of the scale reference markings uniquely corresponding to a particular distance to the fixed reference point.

3. The device of claim 2 wherein the scale reference markings comprise a sequentially increasing marker series at selected intervals distributed therealong the proximal portion of the wire guide.

4. The device of claim 2 wherein the scale reference markings include a progressively increasing series of markings, each member of the series corresponding to a particular distance to the fixed reference point with each of the members being located at 5 cm increments with respect to any adjacent members of the series.

5. The device of claim 2 wherein the scale reference markings include numerical values identifying the particular distance to the fixed reference point.

6. The device of claim 5 wherein the first system of indicia further includes a plurality of intermediate markings located therebetween selected adjacent scale reference markings.

7. The device of claim 1 wherein the distal portion includes at least one radiopaque marker.

8. The device of claim 7 wherein one of the at least one radiopaque marker includes the distal tip.

9. The device of claim 1 wherein the second system of indicia includes a pluarlity of oblique markings.

10. The device of claim 1 wherein the second system of indicia comprises a series of discrete diagonal lines that at least partially circumscribe the wire guide.

11. The device of claim 10 wherein the second system of indicia comprises at least on helical stripe extending along at least a portion of the wire guide.

12. The device of claim 10 wherein the wire guide further includes an outerlayer, the outer layer including alternating first and second helical striping incorporated thereinto.

13. A medical device for measuring an anatomical structure comprising a first reference and a second reference within a body passage during a medical procedure which uses an endoscope, comprising:

a wire guide that includes a distal tip, a distal portion having at least one radiopaque marker, a proximal portion and a fixed reference point, wherein the proximal portion includes at least a first system of indicia that includes a plurality of uniquely identifiable scale reference markings comprising at least two different types of markings which are at least partially viewable while the distal portion of the wire guide as viewed with the endoscope is positioned relative to the first reference of the anatomical structure to obtain a first measurement, and the plurality of uniquely identifiable scale reference markings on the proximal portion are at least partially viewable while the distal portion of the wire guide as viewed with the endoscope is positioned relative to the second reference of the anatomical structure to obtain a second measurement, to thereby measure the anatomical structure within the body passage by comparing the first measurement with the second measurement, wherein the first system of indicia comprises both the uniquely identifiable scale reference markings and a plurality of intermediate markings located between selected ones of the uniquely identifiable scale reference markings, the wire guide further including a second system of indicia comprising a pattern of markings that permit continuous monitoring of movement of the device by the operator thereof.

14. The device of claim 13 wherein the indicia sufficiently circumscribe the distal portion to assuredly be at least partially viewable within the viewing region at any angular position of the elongate member.

15. The device of claim 13 wherein the scale reference markings comprise a sequentially increasing marker series.

16. The device of claim 15 wherein the sequentially increasing marker series comprises differently numbered bands at least partially circumscribing the wire guide.

17. The device of claim 13 wherein the scale reference markings are located at 5 cm increments relative to the fixed reference point, and the intermediate markings are located at 1 cm increments relative to the fixed reference point.

18. A medical device for measuring an anatomical structure comprising a first reference and a second reference within a body passage, comprising:

a wire guide comprising a distal portion;

a plurality of uniquely identifiable scale reference markings comprising at least two different types of markings distributed along at least a portion of the distal portion, at least a portion of the uniquely identifiable scale reference markings comprising numeric indicia, at least a portion of the uniquely identifiable scale reference markings distributed along the distal portion of the wire guide is viewable to an operator with an endoscope while the distal portion of the wire guide as viewed with the endoscope is positioned relative to the first reference of the anatomical structure to obtain a first measurement, and at least a portion of the uniquely identifiable scale reference markings distributed along the distal portion of the wire guide is viewable to the operator with the endoscope while distal portion of the wire guide as viewed with the endoscope is positioned relative to the second reference of the anatomical structure such that the anatomical structure within the body passage can be measured by comparing the first measurement to the second measurement, and a pattern of markings that permit continuous monitoring of movement of the device by the operator thereof.

19. The device of claim 18 wherein the wire guide comprises a solid core wire with a polymeric outer coating, the numeric indicia imprinted on the outer coating.

20. The device of claim 18 wherein the at least a portion of adjacent ones of the numeric indicia are located at 1 cm intervals with respect to one other.

21. The device of claim 20 wherein the scale reference markings further include a series of a sequentially increasing numbered bands between selected ones of the numeric indicia.

22. The device of claim 18 wherein the distal portion further includes a radiopaque marker.

23. A medical device for measuring an anatomical structure having a first reference and a second reference within a body passage during a medical procedure which uses an endoscope, comprising:

a wire guide comprising a solid inner core and an outer coating, the wire guide including a distal tip, a distal portion that includes at least one radiopaque marker, a proximal portion, and an indicia pattern;

wherein the indicia pattern, which is at least partially located on the proximal portion, includes a first system of indicia that includes a plurality of uniquely identifiable scale reference markings comprising at least two different types of markings and a fixed reference point, the plurality of uniquely identifiable scale reference markings comprising a sequentially increasing marker series located at 5 cm intervals from the fixed reference point, the first system of indicia further including numeric indicia located at 1 cm increments between selected ones of the sequentially increasing marker series;

wherein at least a portion of the first system of indicia is viewable to an operator of the medical device as the wire guide proximal of the distal portion is situated in the endoscope during the medical procedure, when the distal portion of the wire guide extends at least partially beyond the distal end of the endoscope;

wherein at least a portion of the first system of indicia is viewable to an operator of the medical device while the distal portion as viewed with the endoscope is positioned relative to the first reference of the anatomical structure to obtain a first measurement, and at least a portion of the first system of indicia is viewable to an operator of the medical device while the distal portion as viewed with the endoscope is positioned relative to the second reference of the anatomical structure to obtain a second measurement, such that the anatomical structure within the body passage can be measured by comparing the first measurement and the second measurement; and the indicia pattern further includes a second system of indicia comprising a pattern of markings that permits continuous monitoring of movement of the device by the operator thereof, the pattern of markings extending along at least a portion of the wire guide, including at least a series of discrete diagonal lines that at least partially circumscribe the wire guide, the pattern of markings further including at least one helical stripe.

* * * * *

UNITED STATES PATENT AND TRADEMARK OFFICE

CERTIFICATE OF CORRECTION

PATENT NO. : 6,613,002 B1
DATED : September 2, 2003
INVENTOR(S) : Tamisha A. Clark et al.

It is certified that error appears in the above-identified patent and that said Letters Patent is hereby corrected as shown below:

Title page,
Item [56], References Cited, OTHER PUBLICATIONS, "Trace® Hybrid;" reference, after "Medical Inc.;" insert -- Catalog; --.

Signed and Sealed this

Eighth Day of March, 2005

JON W. DUDAS
*Director of the United States Patent and Trademark Office*